United States Patent
Chuang

(10) Patent No.: US 8,226,550 B2
(45) Date of Patent: Jul. 24, 2012

(54) CAPSULE ENDOSCOPE

(75) Inventor: Hsin-Hung Chuang, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 591 days.

(21) Appl. No.: 12/495,780

(22) Filed: Jun. 30, 2009

(65) Prior Publication Data

US 2010/0094084 A1   Apr. 15, 2010

(51) Int. Cl.
  *A61B 1/00* (2006.01)
  *A61B 1/04* (2006.01)
  *A61B 1/06* (2006.01)
(52) U.S. Cl. ......... 600/160; 600/176; 600/130; 600/101
(58) Field of Classification Search .............. 600/101, 600/160, 109, 178, 176, 130
See application file for complete search history.

(56) References Cited

U.S. PATENT DOCUMENTS

| | | | | |
|---|---|---|---|---|
| 3,719,183 A * | 3/1973 | Schwartz | | 600/302 |
| 6,119,031 A * | 9/2000 | Crowley | | 600/407 |
| 7,485,093 B2 * | 2/2009 | Glukhovsky | | 600/160 |
| 7,536,217 B2 * | 5/2009 | Minai et al. | | 600/424 |
| 7,647,090 B1 * | 1/2010 | Frisch et al. | | 600/473 |
| 7,869,856 B2 * | 1/2011 | Refael | | 600/407 |
| 8,055,329 B2 * | 11/2011 | Kimchy et al. | | 600/436 |
| 2004/0162469 A1 * | 8/2004 | Imran | | 600/310 |
| 2004/0193023 A1 * | 9/2004 | Mardirossian | | 600/309 |
| 2006/0004255 A1 * | 1/2006 | Iddan et al. | | 600/160 |
| 2007/0282164 A1 * | 12/2007 | Frisch et al. | | 600/109 |
| 2010/0137686 A1 * | 6/2010 | Meron et al. | | 600/118 |
| 2011/0065983 A1 * | 3/2011 | Hafezi et al. | | 600/101 |

* cited by examiner

*Primary Examiner* — John P Leubecker
(74) *Attorney, Agent, or Firm* — Altis Law Group, Inc.

(57) ABSTRACT

A capsule endoscope includes a housing, a lens module, a light source, an imaging module, a memory, a radio frequency transmitter, a power source, and a chamber. The lens module is received in the housing. The light source is configured for illuminating an interior of a body. The imaging module is configured for capturing images of the interior of the body. The memory is configured for storing the captured images. The radio frequency transmitter is configured for wirelessly transmitting the stored images. The power source is electrically connected to the imaging module, the memory and the radio frequency transmitter. The chamber is received in the housing. The lens module and the housing are made of a biodegradable material, and the chamber, the light sources, the imaging module, the memory, the power source, and the radio frequency transmitter are made of a non-biodegradable material.

16 Claims, 1 Drawing Sheet

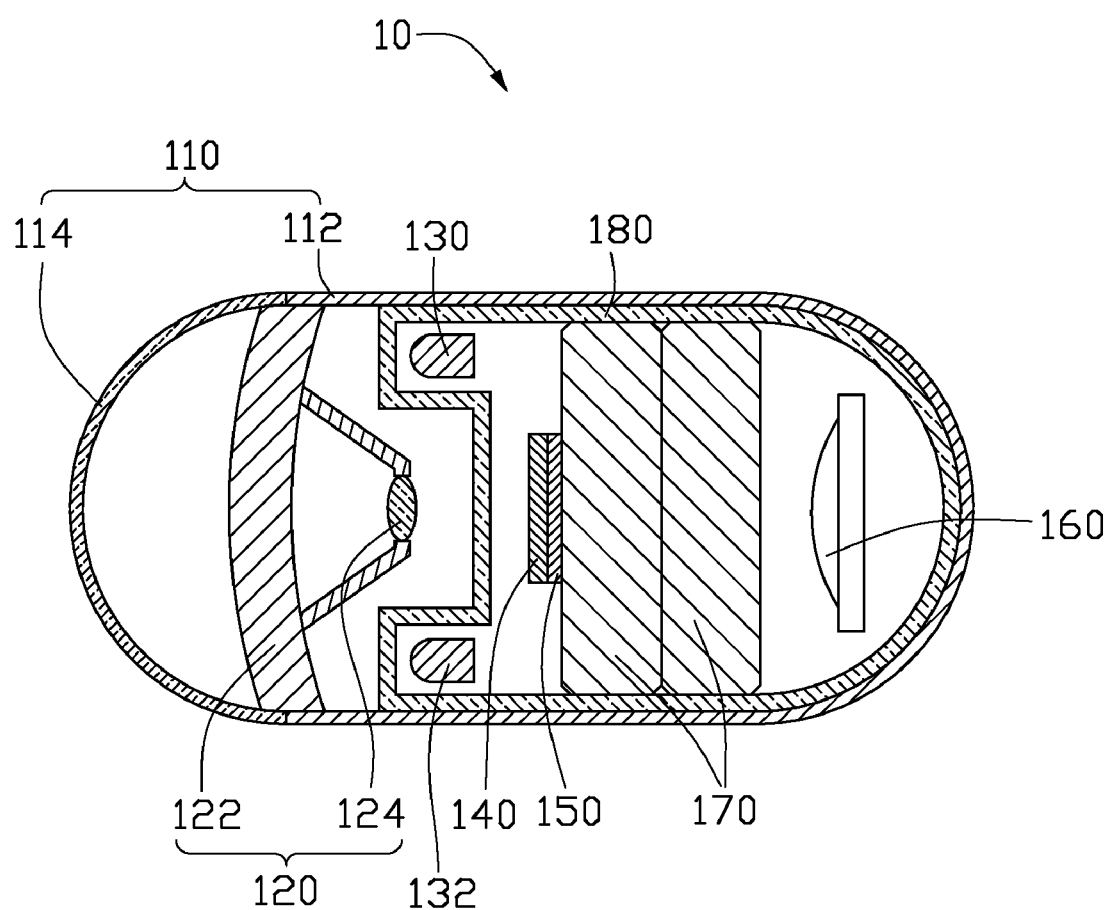

CAPSULE ENDOSCOPE

BACKGROUND

1. Technical Field

The disclosure relates to endoscopes, and particularly, to a capsule endoscope.

2. Description of Related Art

Generally, the capsule endoscope is used to visualize the digestive system, such as the small intestine. However, the digestive system is very long and very convoluted, especially when the small intestine is narrow, common capsule endoscope is difficult to travel in small intestine and excrete.

Accordingly, it is desirable to provide a capsule endoscope, which can overcome the above-mentioned problem.

BRIEF DESCRIPTION OF THE DRAWINGS

The drawing is an schematic sectional view of a capsule endoscope according to an exemplary embodiment.

DETAILED DESCRIPTION

Embodiments of the disclosure will now be described in detail with reference to the accompanying drawings.

Referring to the drawing, a capsule endoscope 10 according to an exemplary embodiment is shown. The capsule endoscope 10 includes a housing 110, a lens module 120, two light sources 130, 132, an imaging module 140, a memory 150, a power source 170, a radio frequency transmitter 160, and a chamber 180. The light sources 130 and 132, the imaging module 140, the memory 150, the radio frequency transmitter 160, and the power source 170 are received in the chamber 180. The lens module 120 and the chamber 180 are received in the housing 110.

The housing 110 is made of a biodegradable material, such as poly DL-Lactic-co-Glycolic acid (PLGA). The PLGA is a polymer of a poly L-lactic acid (PLA) and a poly Glycolic acid (PGA). The shape of the housing 110 is substantially an ellipsoid. The housing 110 includes a main body 112 and a transparent cap 114. The transparent cap 114 is aligned with the lens module 120 for widening the view of the imaging module 140. The transparent cap 114 is made of a transparent and biodegradable resin, such as PLGA.

The lens module 120 is received in the housing 110 and positioned closely to the transparent cap 114. The lens module 120 includes a holder 122 and a lens 124 disposed on the holder 122. The holder 122 and the lens 124 are made of a biodegradable material.

The light sources 130, 132 are received in the chamber 180 and adjacent to the lens module 120. In this embodiment, the light sources 130, 132 are light emitting diodes.

The imaging module 140 is configured for capturing an image. The imaging module 140 is configured for converting light transmitted through the lens 124 to corresponding images. The imaging module 140 typically includes a charge-coupled device (CCD) or a complementary metal oxide semiconductor (CMOS) device.

The memory 150 is configured for storing the images captured by the imaging module 140. In this embodiment, the memory 150 and the imaging module 140 are integrated on a flexible print circuit board (FPCB).

The radio frequency transmitter 160 is configured for receiving the images stored in the memory 150 and transmitting the images wirelessly to an electronic device, such as such as a diagnosing device.

The power source 170 is electrically connected to the imaging module 140, the memory 150, and the radio frequency transmitter 160. In this embodiment, the power source module 170 is a battery, such as a rechargeable battery, a lithium battery or silver chloride battery.

The chamber 180 is made of a non-biodegradable material. In this embodiment, the chamber 180 is a transparent film having smooth surfaces. The smooth surface of the chamber 180 is helpful for the chamber 180 to travel in the digestive system after the housing 110 is biodegraded.

When the capsule endoscope 10 travels through a digestive system of a patient, the imaging module 140 captures a number of images of the digestive system when the digestive system is illuminated by the light sources 130, 132. The images are stored in the memory 150. The radio frequency transmitter 160 transmits the images to an outer device. The housing 110 and the lens module 120 are biodegraded after the capsule endoscope 10 travels from esophagus, small intestine to large intestine. In this embodiment, the housing 110 and the lens module 120 are biodegraded when the capsule endoscope 10 is swallowed after 12 hours. After the housing 110 and the lens module 120 are biodegraded, the chamber 180 housing the imaging module 140, the memory 150, the radio frequency transmitter 160, and the power source 170 may be excreted by a person. It understood that a human body contains enzymes that can dissolve and excrete the above mentioned components.

Alternatively, the housing 110 and the lens module 120 of the capsule endoscope 10 can be biodegraded after the capsule endoscope 10 travels in the digestive system, so that the volume of the capsule endoscope 10 becomes very small. That is, the housing 180 carries the imaging module 140, the memory 150, the radio frequency transmitter 160, and the power source 170 to exit from the digestive system, thereby the capsule endoscope 10 is easy to travel in digestive system and excrete from the body.

It is to be understood, however, that even though numerous characteristics and advantages of the embodiments have been set forth in the foregoing description, together with details of the structures and functions of the embodiments, the disclosure is illustrative only, and changes may be made in detail, especially in matters of arrangement of parts within the principles of the invention to the full extent indicated by the broad general meaning of the terms in which the appended claims are expressed.

What is claimed is:

1. A capsule endoscope for visually examining an interior of a body, comprising:
   a housing;
   a lens module received in the housing;
   a light source configured for illuminating an interior of the body;
   an imaging module configured capturing images of the interior of the body;
   a memory configured for storing the captured images;
   a radio frequency transmitter configured for wirelessly transmitting the stored images;
   a power source electrically connected to the imaging module, the memory and radio frequency transmitter;
   a chamber received in the housing and receiving the light source, the imaging module, the memory, the power source, and the radio frequency transmitter therein;
   wherein the lens module and the housing are made of a biodegradable material, and the chamber, the light sources, the imaging module, the memory, the power source, and the radio frequency transmitter are made of a non-biodegradable material.

2. The capsule endoscope of claim 1, wherein the biodegradable material is poly DL-Lactic-co-Glycolic acid.

3. The capsule endoscope of claim 1, wherein the shape of the housing is substantially an ellipsoid.

4. The capsule endoscope of claim 1, wherein the housing comprises a main body and a transparent cap aligned with the lens module.

5. The capsule endoscope of claim 4, wherein the transparent cap is made of a transparent and biodegradable resin.

6. The capsule endoscope of claim 5, wherein the transparent cap is made of poly DL-Lactic-co-Glycolic acid.

7. The capsule endoscope of claim 4, wherein the lens module is adjacent to the transparent cap of the housing.

8. The capsule endoscope of claim 1, wherein the light source is adjacent to the lens module.

9. The capsule endoscope of claim 1, wherein the light source comprises light emitting diodes.

10. The capsule endoscope of claim 1, wherein the power source module is a battery.

11. The capsule endoscope of claim 1, wherein the power source is a rechargeable battery.

12. The capsule endoscope of claim 1, wherein the power source is a lithium battery.

13. The capsule endoscope of claim 1, wherein the power source is a silver chloride battery.

14. The capsule endoscope of claim 1, wherein the lens module comprises a holder fixed to the housing and a lens held by the holder.

15. The capsule endoscope of claim 14, wherein the holder and the lens are made of a biodegradable material.

16. The capsule endoscope of claim 15, wherein the holder and the lens are made of poly DL-Lactic-co-Glycolic acid.

* * * * *